United States Patent [19]

Schadenberg et al.

[11] 4,212,751
[45] Jul. 15, 1980

[54] DITHIOPHOSPHORIC ACIDS AND SALTS THEREOF AND OIL COMPOSITIONS CONTAINING THE SALTS

[75] Inventors: Hendrik Schadenberg; Corrie M. J. Leenaars; Aaldert J. de Jong, all of Amsterdam, Netherlands

[73] Assignee: Shell Oil Company, Houston, Tex.

[21] Appl. No.: 883,761

[22] Filed: Mar. 6, 1978

[30] Foreign Application Priority Data

Mar. 18, 1977 [GB] United Kingdom ............... 11586/77

[51] Int. Cl.$^2$ ......................... C10M 7/46; C07F 9/177
[52] U.S. Cl. .............................. 252/32.7 E; 260/958; 260/963

[58] Field of Search ..................... 260/958, 963, 429.9; 252/32.7 E

[56] References Cited

U.S. PATENT DOCUMENTS

| 2,368,000 | 1/1945 | Cook et al. ...................... 260/963 X |
| 2,802,856 | 8/1957 | Norman et al. .................. 260/963 X |
| 3,073,857 | 1/1963 | Millikan et al. ................. 260/963 X |

Primary Examiner—Anton H. Sutto
Attorney, Agent, or Firm—Ronald R. Reper

[57] ABSTRACT

Novel esters of dithiophosphoric acid and secondary alcohols having two beta quaternary carbon atoms, and salts of such esters suitable as additives in oil compositions are disclosed.

8 Claims, No Drawings

DITHIOPHOSPHORIC ACIDS AND SALTS THEREOF AND OIL COMPOSITIONS CONTAINING THE SALTS

BACKGROUND OF THE INVENTION

The invention is concerned with novel diesters of dithiophosphoric acids and their salts, a process for the preparation thereof and with oil compositions containing such salts.

It is known to add compounds to oils in order to improve the load-bearing properties, e.g., extreme-pressure and/or anti-wear properties, thereof.

One class of such compounds are the metal salts, such as the polyvalent metal salts, of 0,0'-dihydrocarbyldithiophosphoric acids, e.g., the zinc salts thereof, which are well known as load-bearing additives for lubricating oils. Such salts may be represented by the general formula:

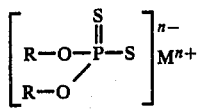

(I)

wherein
R is the same or different optionally substituted hydrocarbyl group,
M is a metal, and
n is the valency of the metal.

Many types of such additives have been proposed, e.g., those in which the R groups represent the same or different alkyl, cycloalkyl, alkylcycloalkyl, aryl, alkaryl and aralkyl groups, e.g., see U.S. Pat. Nos. 2,410,642 and 2,540,084 U.K. Pat. Nos. 723,133 and 852,365. Of these proposals it appears as if two types have achieved some commercial success, namely, the zinc salts of 0,0'-dialkyl- and 0,0'-di(alkaryl)dithiophosphoric acids. Specific examples include the zinc salts of 0,0'-di(2-ethylhexyl)- and 0,0'-di(para-$C_9$/$C_{12}$phenyl)di-thiophosphoric acids. Generally, such known salts either provide inadequate cam wear or pitting protection and/or are insufficiently thermally stable.

SUMMARY OF THE INVENTION

The Applicants have now discovered a novel class of additives which are derived, at least in part, from alcohols, e.g., secondary alcohols, having two beta quarternary carbon atoms. Such secondary alcohols have the structure

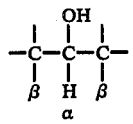

(II)

wherein both beta carbon atoms are quarternary carbon atoms, i.e., none of the substituents on the beta-carbon atoms are hydrogen atoms. Suitably all of the substituents on the beta-carbon atoms are carbon atoms. Additives derived from such alcohols have good thermal stability.

The invention is particularly concerned with the dithiophosphoric acid diesters and salts of such alcohols.

Accordingly, the present invention is concerned with a compound of general formula:

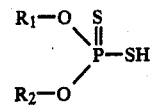

(III)

wherein $R_1$ is a hydrocarbyl group bound to the oxygen atom by a carbon atom having two beta quaternary carbon atoms, and $R_2$ is $R_1$ or a different hydrocarbyl group, which groups $R_1$ and $R_2$ may be substituted by chlorine, hydroxy or ether groups; or a salt thereof.

The invention further provides oil compositions comprising a major amount of an oil and a minor amount of a metal salt of the dithiophosphoric acid diesters according to the invention.

DESCRIPTION OF PREFERRED EMBODIMENTS

The salt may be a monovalent metal such as a Group I metal, in particular an alkali-metal, e.g., sodium or potassium salt or, preferably, a polyvalent metal such as a Group II metal, e.g., magnesium, calcium, barium, zinc or mercury salt. However, other metal salts may be considered such as the salts of aluminum, lead, tin, chromium, manganese, iron, cobalt and nickel. The preferred novel compounds are the zinc salts which may be represented by the general formula:

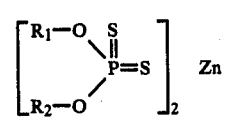

(IV)

wherein $R_1$ and $R_2$ are as hereinbefore defined.

The hydrocarbyl groups of the above compounds contain up to about 18 carbon atoms and preferably up to 15 carbon atoms and may be substituted, e.g., by chlorine, hydroxy or ether groups. Preferably $R_1$ is an aliphatic group such as an alkyl group or, more preferably, a cycloalkyl group bound to the oxygen atom by a ring carbon atom. Examples of suitable alkyl groups include 2,4-tetramethyl-3-pentyl and 2,4-tetramethyl-3-hexyl groups. The cycloalkyl group may be mono-, di-, or tricyclic. Examples include; 1,5-dialkylbicyclo[3,2,1]oct-8-yl; 1,4,4,7 - tetramethyltricyclo[5,3,1,0$^{2,6}$]undec-11-yl(apollan-11-yl) and 1,3,3-trimethylbicyclo[2,2,1]heptan-2-yl)fenchyl). Suitable alkyl substituents of these cycloalkyl groups are $C_1$–$C_4$ alkyl groups in particular methyl groups. The most preferred $R_1$ group is the 1,5-dimethylbicyclo[3,2,1]oct-8-yl group, i.e., a group of formula:

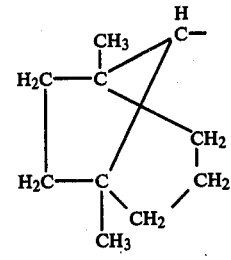

(V)

Preferably, $R_2$ is the same group as $R_1$ but may also be a different optionally substituted hydrocarbyl group such as an alkyl group, e.g., a $C_1$ to $C_{12}$ alkyl group, an aryl group, e.g., phenyl, an alkaryl group, e.g., a $C_5$ to $C_{15}$ alkylphenyl group, an aralkyl group, e.g., benzyl or a cycloalkyl group, e.g., cyclohexyl; such groups not being bound to the oxygen atom by a carbon atom having two beta quarternary carbon atoms.

A particularly preferred novel compound is the zinc salt of O,O'-di(1,5-dimethylbicyclo[3,2,1]oct-8-yl) dithiophosphoric acid.

The novel compounds of the present invention may be prepared by any convenient process. For example, the process may comprise reacting an alcohol, suitably a secondary alcohol, having two beta quaternary carbon atoms and, optionally, one or more different alcohols and/or phenols, with phosphorus pentasulphide to form a diester of dithiophosphoric acid and, optionally, forming a salt from the diester. The diester forming reaction is suitably carried out at elevated temperature, e.g., at a temperature of from 100° to 180° C. As will be clear from the above description of the $R_1$ groups, the preferred alcohols having two quaternary carbon atoms are alkanols or cycloalkanols. Specific examples include; 1,4,4,7-tetramethyltricyclo[5,3,1,0$^{2,6}$]undecan-11-ol(apollan-11-ol); or 1,5-dimethylbicyclo[3,2,1]octan-8-ol. The last mentioned alcohol is particularly suitable since it may easily be prepared by the acid catalyzed hydration and rearrangement of the dimer of isoprene. A single alcohol may be used in which case the above $R_1$ and $R_2$ groups will be the same or the alcohol may be used in admixture with a different alcohol and/or phenol, corresponding to the alcohol or phenol of the $R_2$ groups described above in which case the $R_1$ and $R_2$ groups will be different. Small amounts of esters other than the O,O'-diesters of dithiophosphoric acid may also be formed in the process.

The novel salts may be prepared by neutralization of the diesters of dithiophosphoric acid with a basic metal compound such as a Group I or Group II hydroxide, carbonate or oxide, e.g., sodium hydroxide or zinc oxide. The metal salt so formed may be converted to a different metal salt by double decomposition thereof with a metal salt such as a chloride or sulphate. For example, the sodium salt formed on neutralization may be converted to the zinc salt by reaction thereof with zinc sulphate. The reaction is preferably carried out in the presence of a solvent, e.g., benzene or toluene and under nitrogen. Reaction temperatures of between 30° and 100° C. are suitable. The salt may be isolated from the reaction product mixture by conventional techniques such as by extraction.

The salts of the present invention, in particular the polyvalent metal salts such as the Group II metal salts described above, e.g., the zinc salts, are particularly useful as oil additives.

According to a preferred aspect of the present invention, an oil composition comprises a major proportion of an oil and a minor proportion of a salt of general formula:

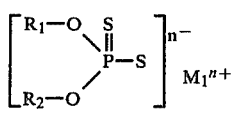

wherein
$R_1$ and $R_2$ are as hereinbefore defined,
$M_1$ is a metal, preferably a polyvalent metal such as a Group II metal, and
n is the valency of the polyvalent metal.

The salts may be added to any oil, e.g., gasoline, middle distillate fuels, industrial oils, greases, etc. but are particularly suitable as additives to oils of lubricating viscosity, especially those for use in internal combustion engines.

Preferably, the oil basestock is a lubricating oil, fractions of a mineral oil such as petroleum, either naphthenic paraffinic or as mixed naphthenic/paraffinic base, unrefined, acid-refined, hydrotreated or solvent refined as required for the particular lubricating need. In addition, synthetic oils such as ester lubricating oils and polyalphaolefins, as well as mixtures thereof with mineral oil meeting the viscosity requirements for a particular application either with or without viscosity index improvers may also be used as basestock provided the above compound is soluble therein. The lubricating oil basestock preferably will have a viscosity in the range from about 5 to about 220 centistokes at 100° F. Suitable mineral oils include low, medium, high and very high viscosity index lubricating oils.

The amount of additive present in the composition may vary between wide limits but is suitably from 0.01 to 10%w, with amounts of from 0.1 to 2%w being usual, based on the weight of the composition.

The lubricating compositions according to the invention may contain other components. Examples of such components include viscosity-index improvers including conjugated diolefin block copolymers and low molecular weight methacrylate polymers, dispersants (of the ash and/or ash-less type), pour-point depressants such as acrylate and methacrylate polymers, anti-oxidants, metal passivators and anti-corrosion agents. If desired, in addition to the present load-bearing additives, the lubricating composition may include other compounds having a load-bearing action.

The invention will now be illustrated with reference to the following Examples.

EXAMPLE 1

55.5 g (0.36 mol) of 1,5-dimethylbicyclo[3,2,1]octan-8-ol was mixed with 20.0 g (0.09 mol) of phophorus pentasulphide and heated for 5 h at 140° C. after which all of the phophorus pentasulphide had reacted. The product, which was a yellow viscous liquid, consisted mainly of O,O'-di(1,5-dimethylbicyclo[3,2,1]oct-8-yl)dithiophosphoric acid.

EXAMPLE 2

45 g of the product prepared in Example 1 was dissolved in 50 ml of toluene. Water (400 ml) was added and the mixture was maintained at 60° C. under nitrogen. The mixture was neutralized with 5 N aqueous NaOH. The reaction product consisted mainly of the sodium salt of O,O'-di(1,5-dimethylbicyclo[3,2,1]octan-8-yl)-dithiophosphoric acid.

EXAMPLE 3

15.9 g (0.06 mol) os zinc sulphate in water was added slowly, with stirring, to the reaction product obtained in Example 2. The reaction was carried out for 1.5 hr at 65° C. The mixture was then extracted with gasoline (b.p. 60° to 80° C.) and the extract was filtered, dried and the gasoline evaporated. The solid residue (39.9 g) which consisted mainly of the zinc salt of O,O'-di(1,5-dimethylbicyclo[3,2,1]octan-8-yl)dithiophosphoric acid had a melting point of 150°–200° C.

| Analysis | C | H | S | Zn |
|---|---|---|---|---|
| Calculated (%) | 55 | 8.5 | 14.5 | 7.43 |
| Found | 57 | 8.26 | 14.22 | 6.75 |

EXAMPLE 4

Lubricating oil compositions were prepared as follows:

| | |
|---|---|
| Qatar Marine base oil (HVI 60) | balance |
| Styrene/hydrogenated butadiene copolymer (VI improver) | 3.2%w |
| Polyisobutylene maleic anhydride/ pentaerythritol adduct (dispersant) | 2.8%w a.m. |
| load-bearing additive | 1.0%w |

Three load-bearing additives were used, namely
(i) product of Example 3 (Example 4):
(ii) zinc salt of O,O'-di(w-ethylhexyl)dithiophosphoric acid (comparative Example (a)): and
(iii) zinc salt of O,O'-di(para-$C_{12}$ phenyl)dithiophosphoric acid (comparative Example (b)).

The oil compositions were tested in a Cam and Tappet Rig. The rig comprises three housings in each of which are rotably mounted cams made from induction hardened cast iron. A tappet, made of chilled cast iron, is in forced contact with each cam. The area of contact between each tappet and rotating cam is lubricated by means of the oil composition which is pumped between each tappet and rotating cam and then allowed to drain from the housing back into the reservoir. During the test the cam rotates at about 1500 revs/min under a static tappet load, when the cam is at top position, of 220 kg.f. The oil temperature is maintained at about 80° C. and about 700 g of oil are used in the test. The test is carried out for a period of 20 hours after which the cam and tappets are replaced and the test continued, using the used oil, for further periods of 20 hours.

The cams are weighed before and after the test and the weight loss of each cam is calculated. The tappets are also visually examined to see whether pitting has occurred. Sometimes, a cam fails completely which can be observed by an increase in oil temperature at the oil outlet port of the housing.

The results are given in Table I.

TABLE I

| Example | Number of Experiments | Average cam wear (mg) | Percentage tappets with pitting |
|---|---|---|---|
| 4 | 6 | 76 | 17 |
| (a) | 6 | 495 | 50 |
| (b) | 6 | 6020 | (1) |

(1) not determined because all cams failed completely.

EXAMPLE 5

10 mg samples of the product of Example 3 were heated under air and nitrogen at a rate of 10° C./minute. The temperatures at which 5%w and 10%w of the sample had been volatilized were noted. The experiment (comparative example (c)) was repeated with additive (ii) of Example 4. The results were as follows:

| | | 5%w | | 10%w | |
|---|---|---|---|---|---|
| Example | Additive | air | nitrogen | air | nitrogen |
| 5 | Example 3 | 240° C. | 232° C. | 250° C. | 248° C. |
| (c) | (ii) | 226° C. | 220° C. | 232° C. | 226° C. |

What we claim is:
1. A compound of general formula:

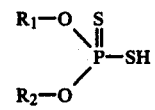

wherein $R_1$ is a 1,5-dimethylbicyclo[3,2,1]oct-8-yl hydrocarbyl group bound to the oxygen by a ring carbon atom having two beta quarternary carbon atoms, and $R_2$ is $R_1$ or a different hydrocarbyl group which $R_2$ group may contain up to about 15 carbon atoms and may be substituted by chlorine, hydroxyl or ether groups, or a Group I or Group II metal salt thereof.

2. Compounds as in claim 1, wherein the salt is a sodium or a zinc salt.

3. Sodium salt of O,O'-di(1,5-dimethylbicyclo[3,2,1]octan-8-yl)dithiophosphoric acid.

4. Zinc salt of O,O'-di(1,5-dimethylbicyclo[3,2,1]octan-8-yl)dithiophosphoric acid.

5. O,O'-di(1,5-dimethylbicyclo[3,2,1]oct-8-yl)dithiophosphoric acid.

6. An oil composition comprising a major proportion of an oil of lubricating viscosity and from 0.01 to 10%w, based on the composition of a salt as in claim 1.

7. An oil composition as claimed in claim 6, wherein the salt is a zinc salt.

8. An oil composition comprising a major proportion of an oil of lubricating viscosity and from 0.01 to 10%w on the composition of the zinc salt of O,O'-di(1,5-dimethylbicyclo[3,2,1]oct-8-yl)dithiophosphoric acid.

* * * * *